United States Patent [19]

Shulze

[11] Patent Number: 5,012,809
[45] Date of Patent: May 7, 1991

[54] FIBER OPTIC CATHETER SYSTEM WITH FLUOROMETRIC SENSOR AND INTEGRAL FLEXURE COMPENSATION

[76] Inventor: John E. Shulze, 1450 Corte de Prima Vera, Thousand Oaks, Calif. 91360

[21] Appl. No.: 917,399

[22] Filed: Oct. 10, 1986

[51] Int. Cl.$^5$ .............................................. A61B 5/00
[52] U.S. Cl. .................................. 128/634; 128/665; 422/52; 436/172
[58] Field of Search .............................. 128/633–634, 128/664, 665, 666; 436/172; 422/52, 55, 56

[56] References Cited

U.S. PATENT DOCUMENTS

| Re. 31,879 | 5/1985 | Lubbers et al. | 128/634 |
| 4,178,917 | 12/1979 | Shapiro | 128/633 |
| 4,476,870 | 10/1984 | Peterson et al. | 128/634 |
| 4,487,206 | 12/1984 | Aagand | 128/634 |
| 4,557,900 | 12/1985 | Heitzmann | 128/665 |
| 4,675,529 | 6/1987 | Kushida | 128/665 |
| 4,752,115 | 6/1988 | Murray et al. | 128/634 |
| 4,810,655 | 3/1989 | Khalil et al. | 128/634 |

FOREIGN PATENT DOCUMENTS 2132348 7/1984 United Kingdom .

OTHER PUBLICATIONS

Kahil et al., PCT No. WO87/00023, Published Jan. 1987, filed 27 Jun., 1986, Priority in U.S. to Jul. 3, 1985.

*Primary Examiner*—Max Hindenburg
*Assistant Examiner*—John C. Hanley
*Attorney, Agent, or Firm*—Stephen J. Schultz

[57] ABSTRACT

A sensor for measuring fluid concentrations or the temperature of body. A fiber-optic catheter having a fluorometric sensor attached at a distal end is excited by a light source outside the body. The sensor fluoresces with an intensity or with a lifetime related to the concentration of the fluid or the temperature. The catheter has one light pipe for exciting the sensor and a second light pipe for generating a reference signal to calibrate signals from the fluorometric sensor. One embodiment has two sensors that fluoresce with different intensities and lifetimes to simultaneously give information about both the temperature and the fluid concentration.

3 Claims, 4 Drawing Sheets

FIBER OPTIC CATHETER SYSTEM WITH FLUOROMETRIC SENSOR AND INTEGRAL FLEXURE COMPENSATION

TECHNICAL FIELD

This invention relates to an in situ measurement of physiological fluid components and more specifically to a fiber optic catheter system including a fluorometric sensor for measuring blood gas concentrations and temperatures and featuring an integral flexure compensator.

BACKGROUND ART

A number of fluorometric sensors suitable or adaptable for use inside the body or in body fluids have been described in the art. Common attributes of these fluorometric sensors are as follows:

(1) A fluophor which fluoresces when irradiated by electromagnetic radiation, the fluorescence being sensitively and substantially quenched by a particular fluid component of interest, and the quenching proceeding theoretically according to the STERN-VOLMER relationship, J. Frank, 9, Z. Phys., 259, (1922); Kautsky, H., 35, Trans. Farady Soc., 216 (1939); Stern and Volmer, 20 Physic. Z., 183 (1919);

(2) A fluid-component permeable, light-transmissive matrix, generally a polymer plastic, which contains, immobilizes and shields the fluorphor from contaminants and interferants found in the body environment; and (3) Means for delivering electromagnetic excitation energy (light) to the matrix and a detector scheme for sensing the fluorescence of the fluorophor, the fluorescence intensity or lifetime changing inversely with the concentration of the fluid component diffusing into the matrix from the surrounding environment. In some of the more recent art, the means comprises light sources and electronic detectors flexibly coupled via fiber optic light pipes, so that the fluorometric sensor can be placed at the tip of a catheter for taking measurements inside blood vessels or in remote areas within the body.

U.S. Pat. No. 3,612,866 describes an instrument for determining oxygen quantities by measuring oxygen quenching of fluorescent radiation employing pyrene or other aromatic compounds (fluophors) embedded in a polymer film and proposes using the instrument for measuring oxygen pressures in blood.

U.S. Pat. No. 3,725,658 discloses a method and apparatus for continuously detecting oxygen in a gas stream employing pyrene or other organic fluorophors quenchable by oxygen dissolved in mineral oil or solid greases.

U.S. Pat. No. Re. 31,879 discloses the use of organic fluophors such as pyrene-butyric acid and beta-methylumbelliferon embedded in rubber, PVC, or other synthetic plastics to form fluometric sensors for oxygen and carbon dioxide, respectively, and teaches the use of such sensors in fiber optic catheters for placement into the bloodstream for fluorometric sensing of pH and blood gas concentrations.

Saari and Seitz describe the construction of a fluorometric pH sensor based on the immobilization of fluoresceinamine on cellulose in 54, Anal. Chem. 821-3 (1982). U.S. Pat. Nos. 4,399,099 and 4,321,057 describe the construction of fluorometric sensors wherein fluoranthrene is embedded in the oxygen-permeable cladding of a fiber optic light pipe. The apparatus of U.S. Pat. Nos. 4,399,099 and 4,321,057 requires the construction of special fiber optic cables with fluophors embedded in gas-permeable claddings.

U.S. Pat. No. 4,476,870 describes the construction of a fiber optic oxygen probe for use in the bloodstream wherein parylene dibutyrate is solvent-diffused into an acrylic plastic substrate to form a moisture-impervious indicator matrix. The matrix is coupled to a remote light source and detector via two fiber optic light pipes.

U.K. patent application No. 2132348A, describes a fluorometric oxygen sensor based upon the solvent diffusion of certain oxygen-quenchable organo-metallic fluophors into polymer films. The preferred embodiment is the solvent diffusion of tris (4,7-diphenyl-1,10-phenanthroline) ruthenium (II) perchlorate into silicone rubber. One proposed use for the sensor is the measurement of oxygen in blood vessels, facilitated by employing coupling fiber optic light pipes.

Cox and Dunn describe a fluorometric oxygen sensor coupled to a bundle of fiber optic light pipes. The sensor is based upon the solvent diffusion of 9,10-diphenyl anthracene into silicone rubber matrixes, in 24 Applied Optics 14 (July 1985).

Each of the foregoing techniques has its own drawbacks and limitations with respect to the construction of a fluorometric sensor for use inside the body.

For instance, the instrument of U.S. Pat. No. 3,612,866 cannot be sufficiently miniaturized for direct insertion into the body, while the instrument of U.S. Pat. No. 3,725,658 is bulky and is designed for measurement in gas streams.

U.S. Pat. Nos. Re. 31,879, 4,399,099 and 4,321,052 and Cox and Dunn utilize fluophors which require ultraviolet light excitation. Fluophors requiring ultraviolet light excitation dictate the use of stiff and relatively expensive fiber optic light pipes constructed of glass. In addition to economic drawbacks, UV-transmitting optics can also fracture when bent tortuously, presenting a safety hazard to the patient when used in catheter applications.

The apparatus described by Saari and Seitz is not suitable for direct tissue implantation because of its physical size, the multiplicity of optical fibers and the requirement that it be placed in a light tight container.

The fiber optic oxygen sensor of U.S. Pat. No. 4,476,870, although overcoming many of the shortcomings of the prior art, is still not suitable for the extreme miniaturization desired in certain catheter applications because of the granular nature of the sensing matrix and the requirement for a separate surrounding membrane.

The fluorometric oxygen sensor of U.K. patent application No. 2132348A employs silicone rubber as the preferred polymer matrix as do the sensors of U.S. Pat. No. Re. 31,879 and of Cox and Dunn. The selection of silicone rubber was based on its unequalled permeability oxygen and carbon dioxide (two fluid components of widespread interest in the analysis of biological systems). Other polymer plastics are mentioned in the prior art as being usable, but less suitable, by virtue of their poorer gas diffusion characteristics For instance, U.K. patent application No. 2132348A describes attempts to use PVC, polystyrene, polycarbonate, and polystyrene in the fabrication of sensors, but reports difficulties in achieving suitable fluophor doping levels because the fluophor and the various plastics are not adequtely soluble in a common solvent system. U.K. patent application No. 2132348A points out that the oxygen Stern-Volmer constant is greater in silicone rubber than in any other polymer tested when the sensor's output change was measured from 100% oxygen to 100% nitrogen.

Fluorometric sensors constructed by embedding a fluophor in silicone rubber have several drawbacks. It is difficult to bond silicone rubber sheets to other plastics using commonly available adhesives 0.001 inch films constructed according to the method of U.K. Patent Application No. 2132348A are flimsy and easily damaged during construction because silicone rubber is not a strong structural material.

Further, none of the prior art has taught how to overcome a major problem encountered when such fluorometric sensors are placed in flexible catheters and coupled to an external light source and detector system via fiber optics—namely, the fiber optic light pipes exhibit changes in attenuation of excitation and fluorescence light in response to flexing of the catheter as might occur during normal movement of the patient and manipulation of the catheter by a physician. This artifact can be interpreted as a change in the fluid-component concentration level within the body.

U.S. Pat. No. 4,487,206 recognizes the problem of flexure in a fiber optic pressure sensing catheter and teaches the splitting of the source excitation light at tip of the catheter into signal and reference paths. This method, however, is not practical for use with a fluorometric sensor, because the fluorescent radiation from the sensor is omnidirectional in nature, and some of the fluorescent radiation inevitably intrudes into the reference path. Also, the construction of the fluorometric sensor itself according to U.S. Pat. No. 4,487,206 would be needlessly large and complex.

Yet another problem with fluorometric sensors which has not been addressed in the prior art is their sensitivity to temperature fluctuations in the fluid or gaseous environment to be measured. Temperature universally affects the fluorescence of the sensor because of the basic nature of the bimolecular quenching phenomenon. Development of temperature compensation methods would greatly increase the utility of such sensors for measurement applications inside the body.

DISCLOSURE OF THE INVENTION

The present invention provides an improved fluorometric sensor with a greater output and sensitivity to changes in output of the fluorescent signal over the physiological fluid concentrations of interest.

An object of the invention is to provide an improved fluorometric oxygen sensor in the form of a monolithic fluophor/polymer matrix that uses visible light excitation and is simply and easily attached or bonded to inexpensive plastic fiber optic light pipes for remote sensing applications such as in catheters.

Another object of the invention is to provide temperature compensation methods and apparatus for fluorometric sensors. Another object of the invention is to provide for an improved fiber optic catheter system incorporating fluorometric sensors, external excitation source and readout device, and integral flexure compensation. The fluorometric sensor consists of a fluophor/polymer matrix combination wherein the fluophor doping levels and the permeability and solubility of the polymer matrix are optimized so that the fluophor produces its maximum fluorescent signal power change over fluid concentrations of physiological interest. The matrix can be constructed in the form of a sheet, a block or a film, and is physically rugged and easily cut and bonded to inexpensive plastic fiber optic light pipes using conventional adhesives for use in remote measurement applications, such as catheters.

A fluorometric oxygen sensor constructed in accordance with the invention may be excited by a light source having radiation in the range of 200-500 nm and yields fluorescence emissions between 600-700 nm in red color spectrum that are detectable by the human eye.

In another embodiment the invention provides a "paired" oxygen sensor that is capable of determining both oxygen pressure and temperature in its environment by virtue of both sensors in the pair being rapidly responsive to temperature and oxygen changes but having differing quench sensitivities for oxygen.

The invention provides an apparatus for measuring the concentrations of bodily fluid components comprising a catheter suitable for insertion into a body and at least one fluorometric sensor at the distal end of the catheter, the sensor is capable of making semi-permeable contact with a bodily fluid and of emitting a fluorescent signal upon excitation. A reference signal is provided from the distal end of the catheter near the fluorometric sensor. Located at the proximal end of the catheter are a light source, a light detector and a reference detector. The light source emits an excitation light having at least one wavelength in the upper visible, or long ultraviolet light spectrum; the light detector detects the fluorescent signal emitted by the fluorometric sensor upon excitation; and the reference detector detects the reference signal from the distal end of the catheter and monitors variations in the light pipe transmission due to flexure of the catheter. A first light conveying path is provided for conveying a first portion of the excitation light from the light source to the fluorometric sensor to generate the fluorescent signal and for conveying a second portion of excitation light from the light source to generate the reference signal and for conveying the fluorescent signal from the fluorometric sensor to the light signal detector. Second light conveying means are provided for conveying the reference signal from the distal end of the catheter to the reference detector. Coupled to the light detector and the reference detector is a normalizing device for normalizing the fluorescent signal to the reference signal. The normalizing device is coupled to computation and display devices for computing and displaying the bodily fluid component concentration from the normalized fluorescent signal.

BRIEF DESCRIPTION OF THE DRAWINGS

FIG. 7 is a table illustrating the output signal of fluorescent sensors fabricated with different polymers.

BEST MODE FOR CARRYING OUT THE INVENTION

Figure 1A:
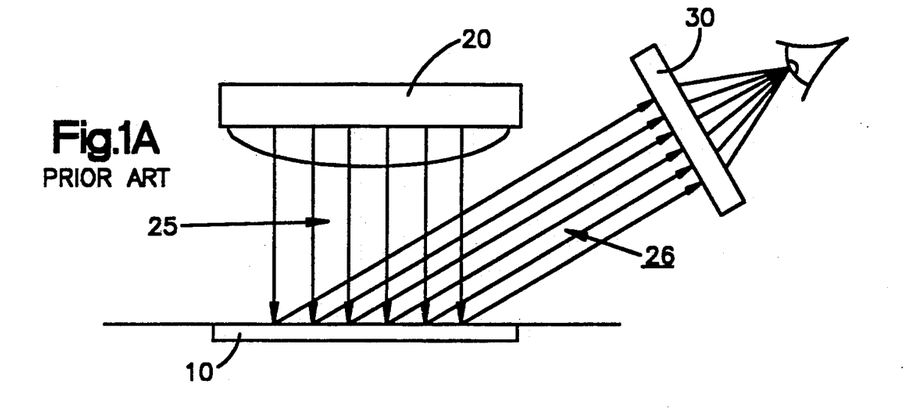
FIG. 1A is a schematic diagram of a prior art oxygen monitoring system having a chemical makeup different from that of the present invention.

FIG. 1A shows a side view of a visual oxygen monitoring system incorporating a fluorometric oxygen sensor 10 constructed according to the present invention. A light source 20 may be a laser, a gas discharge lamp, an incandescent lamp, a laser diode or a visible light emitting diode, such as Siemens #LDB-5410, (Siemens Optoelectronics Corporation). The light source 20 must have at least part of its output wavelengths in the spectrum which excites a fluophor, typically in the upper end of the visible spectrum, (i.e., 400–500 nm). The Siemens LED is particularly advantageous as a source because of its low cost, high efficiency, small size, and uniform output characteristics. An output light 25 from the light source 20 strikes the fluorometric sensor 10, which is located in the environment in which oxygen is to be measured. A resulting fluorescent emission 26 of the sensor emanates in all directions, but at least a portion of the emission travels through a filter 30 and viewed by an observer. The filter 30 improves constrast by allowing only the specific wavelengths of the fluorescent emissions to pass, while blocking scattered light 25 from the source 20, so that the eye can easily determine the changes in fluorescent output of the fluorometric sensor 10 which are the results of changes in the oxygen concentration in the sensor's environment.

The sensor 10 is in the form of a disc of polymeric material into which the fluophor has been dissolved, diffused, or embedded. This disc is formed by mechanical punching from sheets of the polymer/fluophor mixture of approximately 0.001''–0.010'' thickness.

The fluorometric oxygen sensor 10 is preferably prepared from a solution of the fluophor tris (4,7-diphenyl-1,10-phenanthroline) ruthenium (II) complex ion, approximately 1% by weight, with a silicone polycarbonate copolymer (Petrarch Systems, No. PS254, available from Petrarch MB, Bristol, Pa.) containing approximatley 45% silicone and 55% polycarbonate by weight. Alternatively a silicone-alpha methylstyrene copolymer (No. PS096 from Petrarch) may also be used as the polymer constituent with very good results.

The fluophor tris (4,7 diphenyl-1-10-phenanthroline) ruthenium II complex ion was selected for its relatively high quantum efficiency and stability in polymer matrixes, its very high quench sensitivity to oxygen (extraordinarily long fluorescence lifetime), and its wide separation between excitation and emission spectra, both of which are in the visible spectrum. To the inventors' knowledge, it is the only $O_2$ quenchable fluophor that can be excited by the blue light emitting diode of Siemens #LDB-5410 which emits light at 480 nm.

The fluophor and the polymer are dissolved in methylene chloride, and are mixed to the desired proportions. The fluophor being present in the amount of about 0.1 to 3% by weight. The mixture can be cast into blocks, sheets, or films. The methylene chloride is evaporated out of the matrix in a bell jar containing methylene chloride vapors. The solvent vapor pressure in the jar is slowly reduced to zero over several hours resulting in a controlled escape of solvent from the matrix, which ensures clear, uniform solid solutions of the fluophor and polymer.

By varying the amount of methylene chloride in the original mix, the thickness of films cast on a flat surface such as "float" glass can be varied from 1 to 10 thousandths of an inch. Thus, the speed of response of the sensor, which is controlled by its thickness, can be varied by the fabrication technique. Unlike silicone rubber, the silicon polycarbonate film does not adhere to glass and can be easily removed for cutting and processing. It has been found that approximately ½–1% by weight of the fluophor in the matrix is optimum. Above 1%, the output change and intensity of the fluophor in this particular matrix begins to decrease due to concentration quenching effects. Below ½%, the output change (Stern-Volmer coefficient) and intensity of the fluophor begins to decrease due to depopulation of fluophor molecules in the matrix. Optimizing the level of fluophor concentration in the matric has not been recognized by the prior art.

The selection of silicone polycarbonate as the best suitable polymer matrix for use with the preferred fluophor was based on experiments which showed that the highest fluorescent output power change could be obtained in polymers with intermediate oxygen permeabilities and solubilities rather than, as previously taught, the highest possible permeabilities and solubilities.

For sensors based upon fluorescence quenching, the highest Stern-Volmer constant is achieved when the fluophor is embedded in a matrix having the highest permeability and solubility to the fluid component of interest. But, as is herein disclosed and contrary to the teachings of the prior art, the selection of a fluophor/polymer matrix with regard to the greatest Stern-Volmer quenching constant or gas permeability rarely results in a construction which yields the greatest change in fluorescent output signal from the sensor over the fluid-component concentration range of interest. It is highly desirable to maximize the change in the sensor's fluorescent signal power so that companion readout instrumentation can be simple and inexpensive.

As can be seen in the table of FIG. 7, the silicone rubber matrix has a lower effective change in output power than silicone polycarbonate, and in fact most of this change occurs below 40 torr of $O_2$ pressure. For physiological measurement applications, the silicone rubber matrix is too oxygen permeable and soluble for the preferred fluophor, and would be selected only for sensors designed to operate exclusively at very low oxygen pressures or where very fast time response is needed, and then at a compromise in sensor fluorescent output power.

At the other extreme, polymers such as high molecular weight PVC, polycarbonate, polyurethane, and polyethylene (without modifiers or plasticizers) have tightly linked matrixes and much lower solubilities for oxygen. As can be seen in FIG. 7, the fluophor glows brightly but is relatively unquenched, even at 120 torr of ambient oxygen pressure. Such a matrix would be most useful for measurement of very high oxygen pressures, certainly above the usual $O_2$ pressures encountered in the body. Silicone polycarbonate undergoes the greatest output power change when the ambient oxygen pressure changes from 60–125 torr of $O_2$ in the body, a range of great interest in the treatment of critically ill patients.

Fluorometric sensors constructed with silicone polycarbonate can be readily bonded to plastic fiber optic light pipes using poly-methylmethacrylate-based glues such as Permabond 240. Low-attenuation plastic fiber-optic light pipes such as Poly-Optical Products #POM-1410, Irvine, Calif., provide high sensor output signals.

The operation of the fluorometric sensor can be described by a modified form of the Stern-Volmer equation:

$$[Q] = K_g \left[ \left( \frac{I_n}{I_{meas}} \right)^N - 1 \right] \quad (1)$$

where:
- $I_n$ = the unquenched intensity or lifetime at a specific operating temperature
- $[Q]$ = Quencher concentration or pressure.
- $I_{meas}$ = the observed intensity or lifetime at that same operating temperature and at a specific quencher concentration.
- $N$ = a linearizing exponent representing the departure from "perfect" Stern-Volmer at the specified sensor operating temperatue.
- $K_g$ = a lumped constant, proportional to the quench sensitivity of the indicator dye, and containing the reciprocal of the polymer diffusion coefficient and a scaling constant chosen such that the resulting quencher value is expressed in the desired units. $K_g$ represents the composite quenching sensitivity of the sensor.

The prior art has not taught how fluorometric sensors might be compensated for varying temperatures in the sensing environment.

It has been discovered, however, that for a specific polymer/fluophor matrix, the values of $I_n$, $K_g$, and $N$ are predictable functions of temperature. These values may be determined from a look-up table, or from a series of mathematical expressions for each parameter.

In the preferred embodiment, these expressions are:

$$I_n(T) = a + b(T-c)^x$$

where:
- a, b, c, x are constants and
- T = temperature in °C;

and $$N(T) = a_1 + b_1 (T-c_1)^{x_1}$$

where:
- $a_1$, $b_1$, $c_1$, and $x_1$ are constants and
- T = temperature in °C.

and $K_g(T) = a_2 e^{\frac{b_2}{T-c_2}}$ where:
- $a_2$, $b_2$, $c_2$ are constants
- T = temperature in °C.

If the above functions are substituted into the modified Stern-Volmer equation (1), a general expression for the sensor's operation over temperature can be written. For instance, where the quencher of interest is oxygen:

$$PO_2 = K_g(T) \left[ \left( \frac{I_n(T)}{I_{meas}} \right)^{N(T)} - 1 \right]$$

Figure 1B:
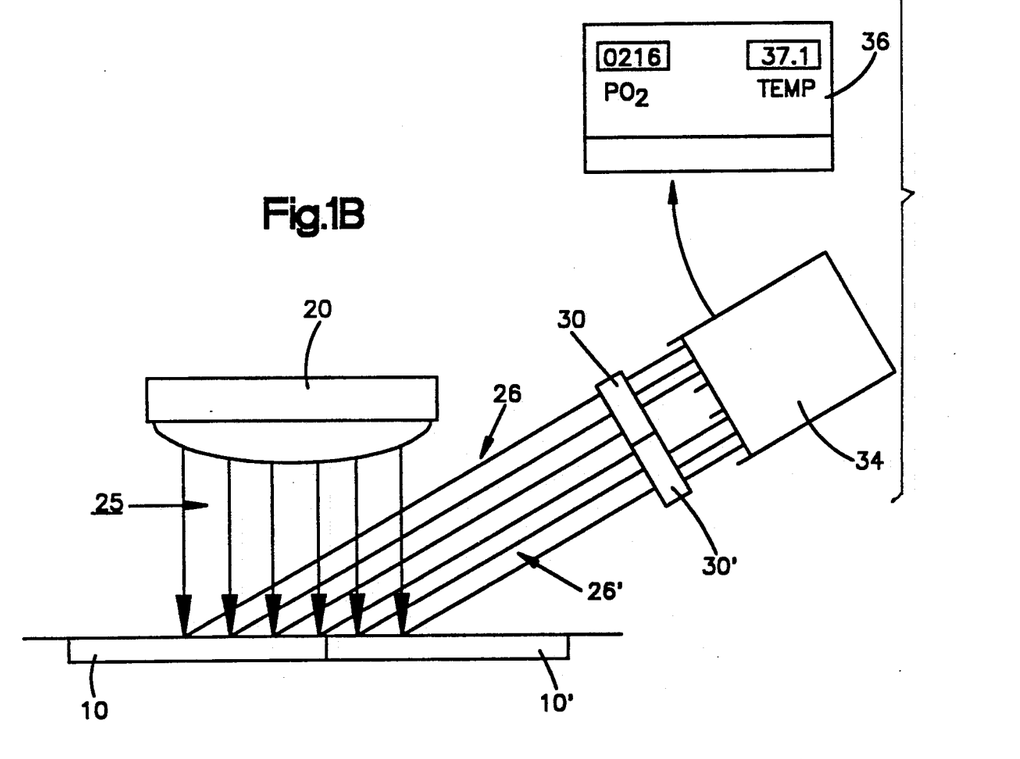
FIG. 1B is a schematic diagram of the oxygen monitoring system with a paired sensor.

Referring now to FIG. 1B, there is shown a "paired" sensor which exploits this mathematical relationship to develop a fluorometric sensor capable of simultaneously measuring both oxygen and temperature in its environment. The successful operation of this sensor requires that the oxygen sensors 10, 10' reside in a common temperature and oxygen sensing environment, and equilibrate relatively rapidly to changes in that environment.

Oxygen sensor 10 ideally has a composite quenching sensitivity, expressed as Kg(T), which is different from that of oxygen sensor 10'. Best measurement resolution is obtained when the KG(T)'s are widely different, e.g., oxygen sensor 10 is a tris (4,7 diphenyl-1,10 phenanthroline) Ru II/silicone-polycarbonate copolymer matrix and oxygen sensor 10' is a tris (4,7 diphenyl1,10 phenanthroline) Ru II/silicone rubber matrix. Alternatively, both sensors can be constructed using silicone-polycarbonate copolymer substrates by the incorporation of dyes having widely differing quench-sensitivities for oxygen, e.g., tris (4,7 diphenyl-1,10-phenanthroline) Ru II for oxygen sensor 10 and tris (bipyridine) Ru II for oxygen sensor 10', which provides for roughly a 10:1 difference in unquenched lifetime and oxygen quench sensitivity. Dissimilar dyes and substrates can also be used without departing from the spirit of the invention, as long as the operation of each sensor as a function of oxygen pressure and temperature can be expressed in equation form.

The temperature and oxygen pressure in the environment of the "paired" sensor can now be determined by the solution of two simultaneous equations:

$$PO_2 = K_{g1}(T) \left[ \left( \frac{I_{n1}(T)}{I_{meas1}} \right)^{N1(T)} - 1 \right]$$

$$PO_2 = K_{g2}(T) \left[ \left( \frac{I_{n2}(T)}{I_{meas2}} \right)^{N2(T)} - 1 \right]$$

where:
- $PO_2$ = oxygen pressure in "paired" sensor environment
- T = temperature in "paired" sensor environment
- $K_{g1}(T)$ and $K_{g2}(T)$ = oxygen quenching sensitivities of oxygen sensors 10 and 10' respectively as a function of temperature
- $I_{n1}(T)$ and $I_{n2}(T)$ = unquenched intensities or lifetimes of oxygen sensor 10 and 10' respectivley as a function of temperature
- $N_1(T)$ and $N_2(T)$ = linearizing exponents of oxygen sensors 10 and 10' respectively as a function of temperature
- $I_{meas1}$ and $I_{meas2}$ = output intensities or lifetimes (the choice must match the expressions of $I_n$ of oxygen sensors 10 and 10' respectively).

Upon illumination by the light 20, the two output signals 26, 26' from the "paired" oxygen sensors 10, 10' are directed through filters 30, 30' to a dual photodector system 34. The dual photodetector 34 measures the lifetimes or intensities of oxygen sensors 10 and 10', and provides an output signal to a computation and display device 36, which utilize the above mathematical relationships to compute oxygen pressure and temperature in the sensor's environment and to display the computed oxygen pressure and temperature.

Figure 2:
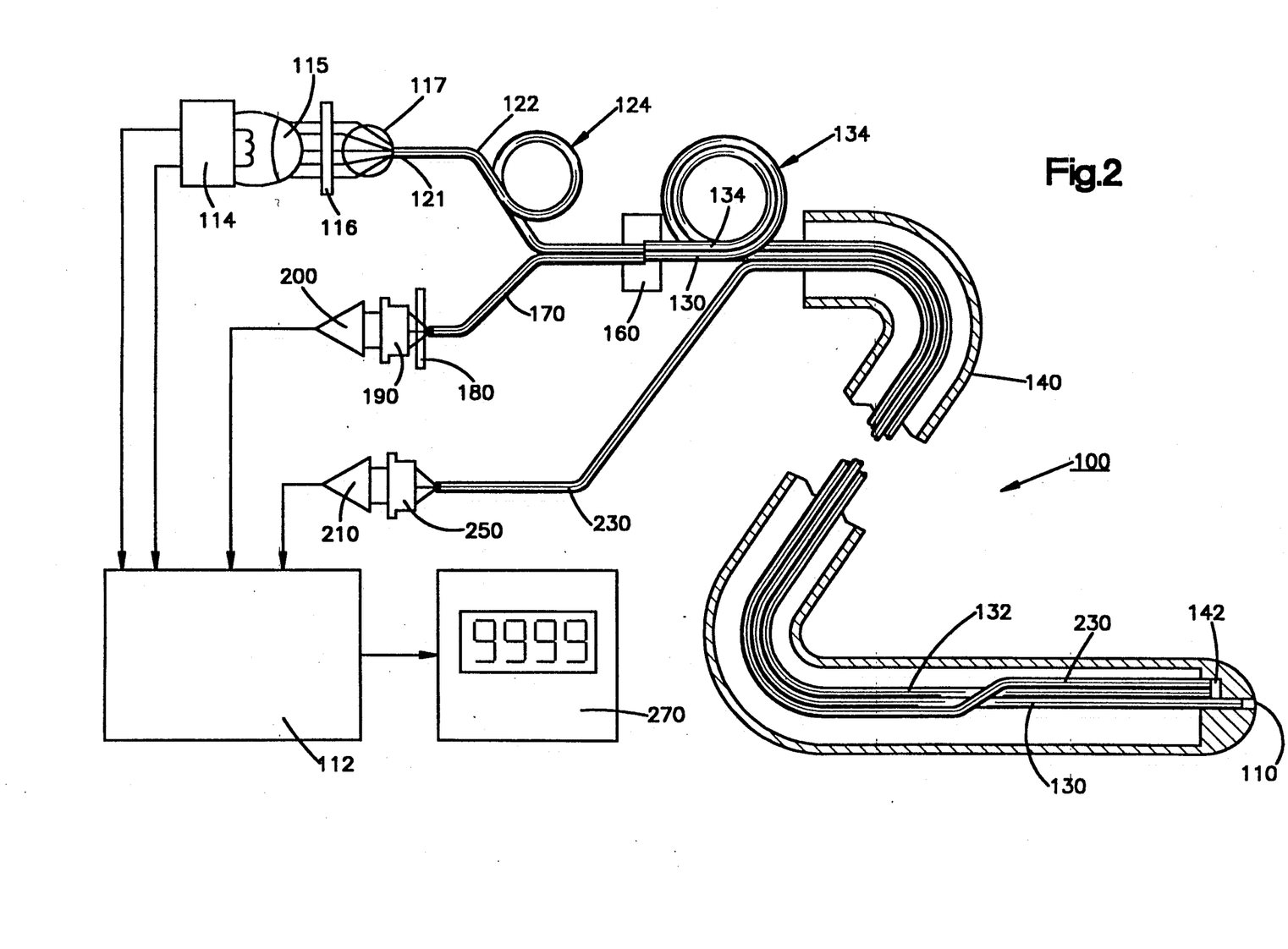
FIG. 2 is a partial, cross-sectional view of a fiber-optic catheter system of the present invention.

FIG. 2 shows a detailed schematic diagram of fiberoptic catheter fluorometric sensor system 100, with a catheter 140. A power supply 112 provides an energizing signal to an incandescent lamp light source 114. Light from the incandescent lamp 114 is partially collimated by an integral lens 115 which directs the light through a short wavelength pass filter 116 and thence into a globe-shaped focusing lens 117 that directs an intense, converging spot of regulated short-wavelength light, to a proximal end 121 of a fiber optic light pipe 122 to a mode scrambler 124.

Figure 4:
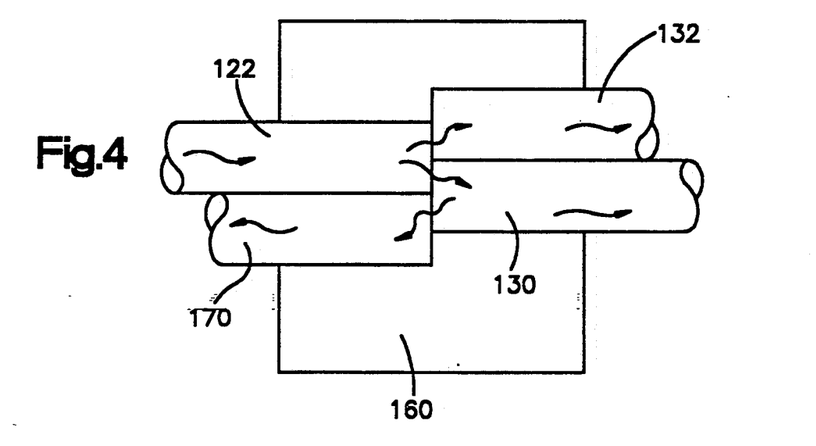
FIG. 4 is a schematic view of a bi-directional splitter used with the catheter systems of FIGS. 2 and 3.

The intense, short-wavelength light exiting the mode-scrambler 124 enters a bi-directional splitter 160, where it is divided or "split" and enters fiber optic light pipes 130, 132 as is best shown in FIG. 4. A portion of the short wavelength light enters the fiber optic light pipe 130 and is ultimately destined to strike a sensor 110 bonded to the flat-polished distal end of the fiber optic pipe 130. A second portion of the short wavelength light enters the fiber optic light pipe 132, which forms the outgoing end of a reference path used to measure properties of the fiber optic light pipe 130. Integral to light pipes 130, 132 is a mode scrambler 134 that provides for uniform distribution of light in all transmission modes.

Although the mode scramblers 124, 134 described herein for clarity are illustrated as single loops it will be understood that in some cases it is desirable to use multiple loops, with the loops located on different axes or planes, and with the loops being made of different diameters in order to accomplish complete and uniform filling of the light transmission modes in the fiber optic light pipes. In accordance with one embodiment of the invention, such mode scramblers are used where it is desirable to achieve maximum immunity to light transmission variations upon flexing the catheter 140. Alternatively, a reasonable level of performance may still be obtained while eliminating mode scramblers 124, 134 altogether, although the measurement accuracy of the system will be somewhat less immune to flexure of the catheter 140.

Figure 6:
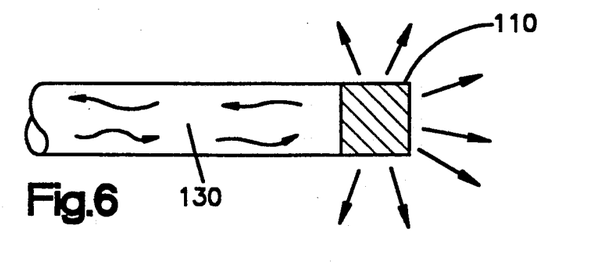
FIG. 6 is a schematic view of the fluorometric sensor located near the tip of the catheter systems of FIGS. 2 and 3.

Short-wavelength light travelling through the catheter in fiber optic light pipe 130, strikes the sensor 110 which is thereby excited to fluorescence as best shown in FIG. 6. The fluorometric sensor 110 is preferably constructed as described herein, or alternatively according to U.K. Patent Application No. 2132348A or U.S. Pat. No. 3,612,866 or the other methods as described in the prior art. A portion of the fluorescence enters the distal end of the fiber optic light pipe 130 and, travels through mode scrambler 134 where any unevenness in transmission modes are removed, and enters bi-directional splitter 160. A portion of the fluorescent light entering the bi-directional splitter from the light pipe 130 is directed to light pipe 170, as is best shown in FIG. 4. This portion of the fluorescent return signal travels via light pipe 170 to a long-pass or a band-pass filter 180 and thence to a photodetector 190 and amplifier 200. Long-pass filter 180 is not rigorously required, but serves to improve the signal-to-noise ratio when using broad-band signal detectors, so that these less expensive components may be used. The electrical signal generated by the amplifier 200, which is proportional to the fluorescent return signal, is sent to the processing unit 112, comprising a power supply, an A/D converter and a microprocessor computer, for comparison with the electrical signal from a reference amplifier 210 described below.

Figure 5:
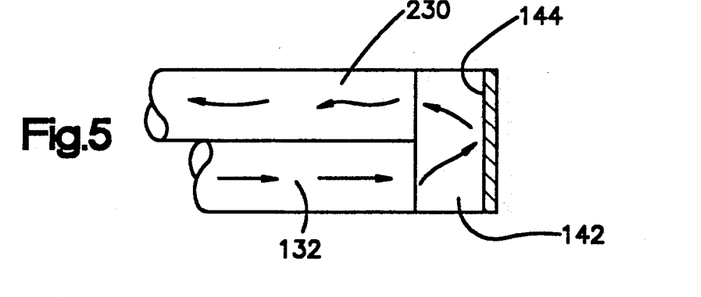
FIG. 5 is a schematic view of a reflector for coupling light located near the tip of the catheter of FIG. 2.

The portion of the short-wavelength light travelling through the fiber optic light pipe 132 and mode scrambler 134 ultimately strikes a reflector 142 as is best shown in FIG. 5. The reflector can be made from a 0.001 to 0.010 inch thick sheet of clear polymer film, such as silicone polycarbonate without the fluophor, bonded to the polished distal ends of the fiber optic light pipes 132, 230. Optionally, a mirrored surface 144 can be deposited on the distal side of the reflector 142 to increase reference path transmission, so that a less sensitive photodetector 250 may be used to measure the strength of the reference signal returning on the fiber optic light pipe 230.

As a third alternative, the reflector 142 can have fluophor embedded in it but be exposed to reference atmospheric gas entering the catheter from its proximal end. In this arrangement the fluorescence of the reflector 142 is observed by reference detector 250, and this "reference fluorescence" intensity is responsive to both catheter flexure and temperature changes in the environment of the fluorometric sensor 110. By this alternative, the single fluorometric sensor 110 can be simultaneously compensated for both temperature variations and flexure via the reference path.

The amplifier 200 output voltage representing the strength of the fluorescence signal is first compared by the processing unit 112 to the amplifier 210 output voltage representing the output power of the source 114 as modified by the dynamic transmission characteristic of the reference path 132, 230 (and therefore the transmission of the fiber optic light pipe 130) to minimize processed signal fluctuations.

The processed or normalized fluorescence signal can then be analyzed by the modified Stern-Volmer equation (I) to correlate the normalized fluorescence signal to the oxygen pressure at the tip of the catheter. The result calculated by the processing unit 112 is displayed at a display 270.

Figure 3:
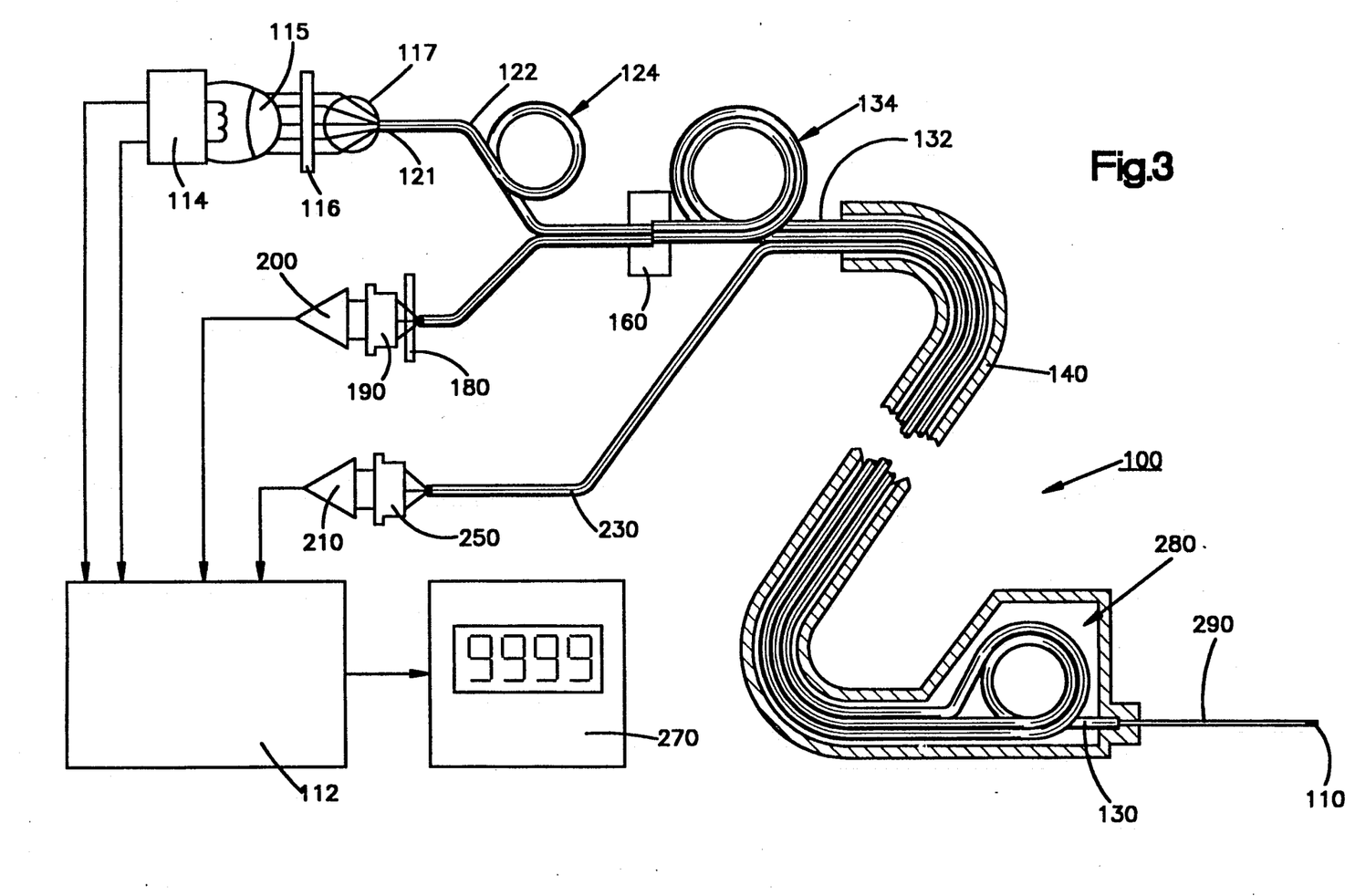
FIG. 3 is a partial cross-sectional view of an alternative construction of a fiber-optic catheter system of the present invention.

A second embodiment, shown in FIG. 3, operates in essentially the same fashion as the embodiment of FIG. 2, except the reflector 142 of FIG. 2 has been replaced with a reference path turnaround loop 280. The catheter 140 serves as an interconnecting means between the electrical portions of the system and a very small, very flexible fiber optic extension catheter 290, which at its most distal end attaches to a fluorometric sensor 110. In addition, fiber optic light pipe 130 is looped at its distal end to form a third mode scrambler. This third mode scrambler reduces uneven transmission of light caused by the junction of light pipes 130 with extension catheter 290. This embodiment is particularly desirable where the extension catheter 290, is to be placed in very small, tortuous vessels such as the radial artery of a human, or a coronary artery. Even through the extension catheter 290, which might be constructed from 0.005-0.010" diameter optical fiber, has very high attenuation, it is very flexible and its attenuation changes little with tortuous bending as might be encountered in these applications. Further, the small diameter of the extension catheter 290 produces minimal trauma to the tissue or organ upon entry and can be constructed as the replaceable or disposable portion of the system. Although unsuitable for use over the greater length of catheter 140, the small diameter extension catheter 290 provides access for measurements of oxygen in very small vessels or chambers, with an inexpensive, sterile, disposable, extension catheter equipped with a fluorometric sensor.

Many modification and variations of the invention will be apparent to those skilled in the art in light of the foregoing detailed disclosure. Therefore, it is to be understood that, within the scope of the appended claims, the invention can be practiced otherwise than as specifically shown and described.

I claim:

1. A fluorometric sensor for measuring oxygen concentration in a body fluid comprising:
   a means for emitting excited light in which at least one wavelength emitted is in the upper visible-long ultraviolet light spectrum;
   an elongated fiber-optic equipped catheter having a distally positioned fluorometric sensor comprising a silicone copolymer matrix and a fluophor formed by dissolving into a silicone copolymer an amount of about 0.1% to 3% by weight of the fluophor selected from the group consisting of parylene dibutyrate, tris (4,7-diphenyl-1,10 phenanthroline) ruthenium II, tris (disulphonated 4,7-diphenyl-1,10 phenanthroline) ruthenium II, and tris (bipyridine) ruthenium II, in order for the fluophor to emit a fluorescent signal in response to the excited light transmitted from a proximal end of the catheter and the fluorescent signal having an intensity that is quenched by oxygen permeating from the body fluid into the silicone copolymer matrix, and wherein the silicone copolymer is selected from the group consisting of silicone polycarbonate copolymer and silicone polystyrene copolymer; and
   means for measuring the intensity of the fluorescent signal from the fluorometric sensor transmitted back to the proximal end of the catheter and for correlating the intensity of the fluorescent signal to the oxygen concentration in the body fluid.

2. A fluorometric sensor for measuring oxygen concentration in a body fluid comprising:
   light excitation means emitting excitation light having at least one wavelength in the upper visible-long ultraviolet light spectrum;
   an elongated fiber-optic equipped catheter including a distally positioned fluorometric sensor comprising a silicone polycarbonate copolymer and an amount of about 0.5% to 1% by weight of a fluophor dissolved into the silicone polycarbonate copolymer that emits a fluorescent signal in response to the excitation light transmitted from a proximal end of the catheter and having an intensity that is quenched by oxygen permeating from the body fluid into the silicone polycarbonate copolymer, and wherein the fluophor is selected from the group consisting of parylene dibutyrate, tris(4,7-diphenyl-1,10 phenanthroline) ruthenium II, tris (disulphonated 4,7-diphenyl-1,10 phenanthroline) ruthenium II, and tris (bipyridine) ruthenium II; and
   means for measuring the intensity of the fluorescent signal from the fluorometric sensor transmitted back to the proximal end of the catheter and for correlating the intensity of the fluorescent signal to the oxygen concentration in the body fluid.

3. A fluorometric sensor for measuring oxygen concentration in a body fluid comprising:
   light excitation means emitting excitation light having at least one wavelength in the upper visible-long ultraviolet light spectrum;
   an elongated fiber-optic equipped catheter including a distally positioned fluorometric sensor comprising a silicone-polystyrene copolymer and an amount of about 0.1% to 3% by weight of a fluophor dissolved into the silicone polystyrene copolymer that emits a fluorescent signal in response to the excitation light transmitted from a proximal end of the catheter and having an intensity that is quenched by oxygen permeating from the body fluid into the silicone polystyrene, and wherein the fluophor is selected from the group consisting of parylene dibutyrate, tris (4,7-diphenyl 1,10 phenanthroline) ruthenium II, tris disulphonated 4,7 diphenyl 1,10 phenanthroline ruthenium II, and tris (bipyridine) ruthenium II; and
   means for measuring the intensity of the fluorescent signal from the fluorometric sensor transmitted back to the proximal end of the catheter and for correlating the intensity of the fluorescent signal to the oxygen concentration in the body fluid.

* * * * *